Dec. 28, 1965 E. B. MARTIN Plant Pat. 2,583
CATTLEYA ORCHID PLANT
Filed Oct. 6, 1964
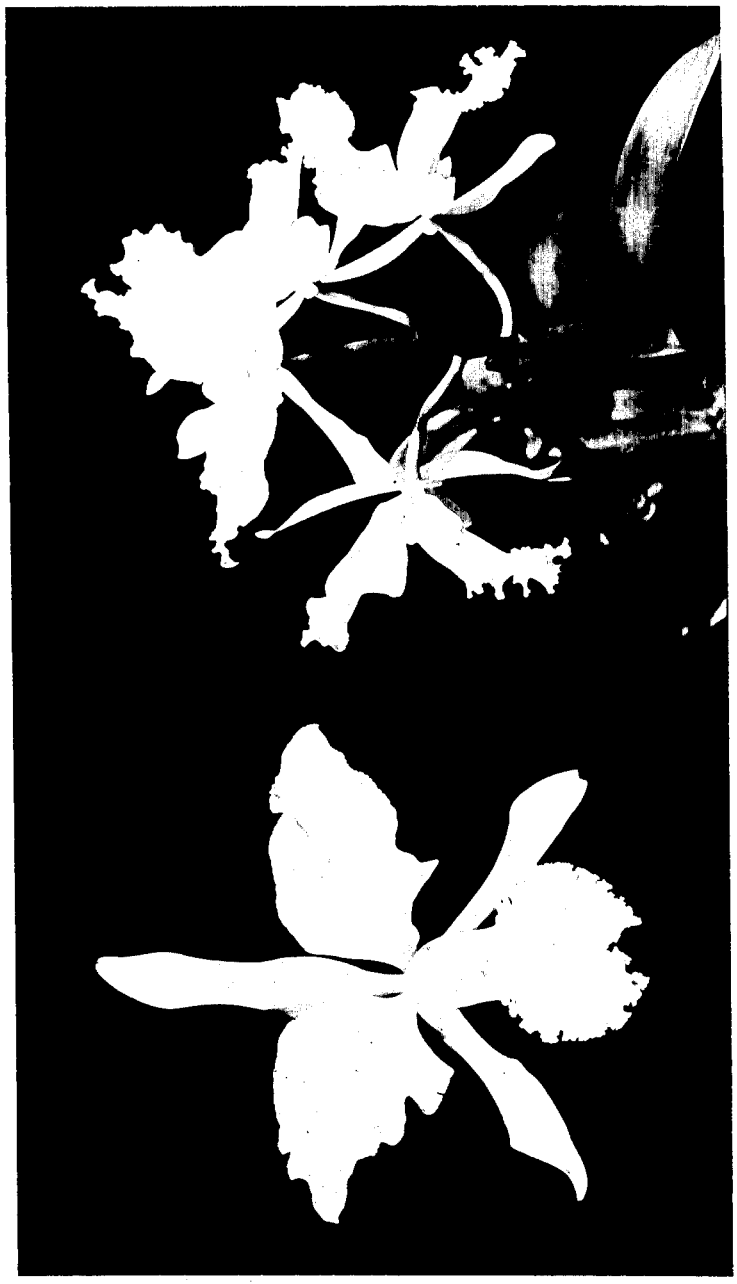
Inventor.
Esmond B. Martin
By: Robb & Robb
Attorneys.

United States Patent Office

Plant Pat. 2,583
Patented Dec. 28, 1965

2,583
CATTLEYA ORCHID PLANT

Esmond B. Martin, Westbury, Long Island, N.Y.

Filed Oct. 6, 1964, Ser. No. 402,044
1 Claim. (Cl. Pit.—68)

The present invention relates to a new and distinct variety of Cattleya orchid plant which was originated by me by crossing the Cattleya variety known as "White Empress" with the Cattleya variety known as "Louise Georgiana" (both unpatented).

The primary objective of this breeding was to improve the flow size, texture and form of the Cattleya variety "Louise Georgiana." This objective was fully achieved along with other desirable improvements, by combining the good qualities of both parent varieties, as evidenced by the following unique combination of characteristics which are outstanding in my new variety and distinguish it from its parents, as well as from all other varieties of which I am aware:

(1) Large flower size;
(2) Superior flower texture;
(3) Excellent cut flower form similar to that of "White Empress";
(4) A flower substance and keeping qualities comparable to those of "Louise Georgiana"; and
(5) A distinctive and attractive almost pure White flower color, with only a slight tint of Pale Yellow color in the throat of the flower which diminishes and substantially disappears as the flower ages.

Asexual reproduction of my new Cattleya orchid variety, as performed by division in my nurseries at Westbury, Long Island, New York, shows that the foregoing characteristics and distinctions are fixed and come true and are transmissible through succeeding propagations.

The accompanying drawing shows a typical specimen plant of my new variety, as well as an individual flower on a somewhat enlarged scale as compared with the view of the plant, all as depicted in color as nearly true as it is reasonably possible to make the same in a color illustration of this character.

The following is a detailed description of my new Cattleya orchid variety, as based on observations of specimens grown at Westbury, Long Island, New York, with color terminology in accordance with Ridgway's Color Standards and Nomenclature, except where general color terms of ordinary dictionary significance are obvious:

Breeding: Hybrid.
*Male parent.*—"White Empress."
*Female parent.*—"Louise Georgiana."

Propagation: Holds its distinguishing characteristics through succeeding propagations by division.

*Plant*

Form: Upright.
Blooming habit: Cluster.
Blooming season: Summer-fall.
Foliage: (mature):
*Size.*—Length—from 10⅜ inches to 12⅜ inches. Width—from 2⅜ inches to 2⅝ inches.
*Habit.*—Single and bifoliate.
*Shape.*—Oblong-pointed.
*Texture.*—Smooth on both upper and under sides.
*Edge.*—Rough.
*Color.*—From Cress Green, Plate 31 to Light Cress Green, Plate 31.

*Flower*

Borne: Usually from 2 to 4 flowers borne in clusters on strong stems.
Form:
*Natural spread.*—7 inches.
*Dorsal sepal.*—Length—3⅝ inches. Width—1 inch.
*Lateral sepals.*—Length—3 inches. Width—1 1/16 inches.
*Petals.*—Length—3½ inches. Width 2½ inches.
*Lip.*—Length—3¼ inches. Width—2⅜ inches.
Color:
*Petals and sepals.*—Pure White.
*Labellum.*—Pure White, with slight touch of Pale Chalcedony Yellow, Plate 27 at the throat.

*Reproductive organs*

Column:
*Color.*—Pure White, with Pale Turtle Green, Plate 32 at base.

I claim:

A new and distinct variety of Cattleya orchid plant, substantially as herein shown and described, characterized particularly as to novelty by the unique combination of a large flower size, superior flower texture, excellent cut flower form similar to that of "White Empress," a flower substance and keeping qualities comparable to those of "Louise Georgiana," and a distinctive and attractive almost pure White flower color, with only a slight tint of Pale Yellow color in the throat of the flower which diminishes and substantially disappears as the flower ages.

No references cited.

ABRAHAM G. STONE, *Primary Examiner.*